United States Patent [19]
Bode et al.

[11] Patent Number: 6,159,722
[45] Date of Patent: Dec. 12, 2000

[54] CHIMERIC SERINE PROTEASES

[75] Inventors: Wolfram Bode, Gauting; Richard Engh, Wessling; Karl-Peter Hopfner, Munich; Robert Huber, Germering; Erhard Kopetzki, Penzberg, all of Germany

[73] Assignee: Boehringer Mannheim GmbH, Mannheim, Germany

[21] Appl. No.: 09/197,801

[22] Filed: Nov. 23, 1998

[30] Foreign Application Priority Data

Dec. 3, 1997 [EP] European Pat. Off. .............. 97121232

[51] Int. Cl.$^7$ .............................. C12N 9/50; C12N 15/00; C12N 9/00
[52] U.S. Cl. ........................... 435/219; 435/23; 435/219; 435/440; 530/350; 530/380; 536/23.2; 536/23.4
[58] Field of Search ............................ 435/219, 23, 440; 536/23.2, 23.4; 530/350, 380

[56] References Cited

FOREIGN PATENT DOCUMENTS

| 0 200 421 | 12/1986 | European Pat. Off. . |
| 0 439 442 | 7/1991 | European Pat. Off. . |
| WO 91/10733 | 7/1991 | WIPO . |
| WO 99/10483 | 3/1999 | WIPO . |
| WO 99/10503 | 3/1999 | WIPO . |

OTHER PUBLICATIONS

Barrett, Proteolytic Enzymes: Serine and Cysteine Peptidases, Methods in Enzymology, vol. 244, pp. 1–15 (1994).
Blow, Structure and Mechanism of Chymotrypsin, Accounts of Chemical Research, vol. 9, pp. 145–152 (1976).
Brandstetter, et al., X–ray Structure of Active Site–inhibited Clotting Factor Xa, The Journal of Biological Chemistry, vol. 271, No. 47, pp. 29988–29992 (1996).
Davie, et al., The Coagulation Cascade: Initiation, Maintenance, and Regulation, Biochemistry, vol. 30, No. 43 pp. 10363–10370 (1991).
Furie, et al., The Molecular Basis of Blood Coagulation, Cell, vol. 53, pp. 505–518 (1988).
Greer, Comparative Modeling Methods: Application to the Family of the Mammalian Serine Protease, Proteins: Structure, Function, and Genetics, vol. 7, pp. 317–334 (1990).
Lesk, et al., Conservation and Variability in the Structures of Serine Proteinases of the Chymotrypsin Family, J. Mol. Biol., vol. 258, pp. 501–537 (1996).
McLachlan, Gene Duplications in the Structural Evolution of Chymotrypsin, J. Mol. Biol., vol. 128, pp. 49–79 (1979).
Padmanabhan, et al., Structure of Human Des(1–45) Factor Xa at 2 2 Resolution, J. Mol. Biol., vol. 232, pp. 947–966 (1993).
Perona, et al., Crystal Structures of Rat Anionic Trypsin Complexed with the Protein Inhibititors APPI and BPTI, J. Mol. Biol., vol. 230, pp. 919–933 (1993).
Perona, et al., Structural basis of substrate specificity in the serine proteases, Protein Science, vol. 4, pp. 337–360 (1995).
Pierard, et al., Mutant and Chimeric Recombinant Plasminogen Activators, Journal of Biological Chemistry, vol. 262, No. 24, pp. 11771–11778 (1987).
Rawlings, et al., Families of Serine Peptidases, Methods of Enzymology, vol. 244, pp. 19–61 (1994).
Stubbs, et al., Crystal structures of factor Xa specific inhibitors in complex with trypsin: structural grounds for inhibition of faxtor Xa and selectivity against thrombin, FEBS Letters, vol. 375, pp. 103–107 (1995).
Twining, Regulation of Proteolytic Activity in Tissues, Critical Reviews in Biochemistry and Molecular Biology, vol. 29, No. 5, pp. 315–383 (1994).

*Primary Examiner*—Rebecca E. Prouty
*Assistant Examiner*—Richard Hutson
*Attorney, Agent, or Firm*—George W. Johnston; William H. Epstein

[57] ABSTRACT

A chimeric serine protease whose protease domain is composed of two domain halves (half-sides) with a β-folded sheet structure, wherein the first domain half corresponds to the first domain half of a first serine protease and the second domain half corresponds to the second domain half of a second serine protease, has improved properties and can be readily crystallized.

3 Claims, 2 Drawing Sheets

Fig. 2

```
NsiI
atgcatcaccaccacgacgatgacgacaagatcGTGGGAGGCCAGGAATGCAAGGACGGG      60
MetHisHisHisHisAspAspAspAspLysIleValGlyGlyGlnGluCysLysAspGly      20
|      Prosegment / AP        |-- FXa -->  QE20YN GAGTGTCCCTGGCAGGCCCTGCTCATCAATGAGGAAAACGAGGGTTTCTGTGGTGGAACC    120
GluCysProTrpGlnAlaLeuLeuIleAsnGluGluAsnGluGlyPheCysGlyGlyThr     40
     C27V ATTCTGAGCGAGTTCTACATCCTAACGGCAGCCCACTGTCTCTACCAAGCCAAGAGATTC    180
IleLeuSerGluPheTyrIleLeuThrAlaAlaHisCysLeuTyrGlnAlaLysArgPhe     60

AAGGTGAGGGTAGGGGACCGGAACACGGAGCAGGAGGAGGGCGGTGAGGCGGTGCACGAG    240
LysValArgValGlyAspArgAsnThrGluGlnGluGluGlyGlyGluAlaValHisGlu     80

GTGGAGGTGGTCATCAAGCACAACCGGTTCACAAAGGAGACCTATGACTTCGACATCGCC    300
ValGluValValIleLysHisAsnArgPheThrLysGluThrTyrAspPheAspIleAla    100

GTGCTCCGGCTCAAGACCCCCATCACCTTCCGCATGAACGTGGCGCCTGCCTCTCTGCCC    360
ValLeuArgLeuLysThrProIleThrPheArgMetAsnValAlaProAlaSerLeuPro    120

Van91I
ACCGCCCCTCCAGCCACTGGCACGAAGTGCCTCATCTCTGGCTGGGGCAACACTGCGAGC    420
ThrAlaProProAlaThrGlyThrLysCysLeuIleSerGlyTrpGlyAsnThrAlaSer    140
                      |-- Trypsin -->    W141F TCTGGCGCCGACTACCCAGACGAGCTGCAGTGCCTGGATGCTCCTGTGCTGAGCCAGGCT    480
SerGlyAlaAspTyrProAspGluLeuGlnCysLeuAspAlaProValLeuSerGlnAla    160

AAGTGTGAAGCCTCCTACCCTGGAAAGATTACCAGCAACATGTTCTGTGTGGGCTTCCTT    540
LysCysGluAlaSerTyrProGlyLysIleThrSerAsnMetPheCysValGlyPheLeu    180
              YPGK172SSFI

GAGGGAGGCAAGGATTCATGTCAGGGTGATTCTGGTGGCCCTGTGGTCTGCAATGGACAG    600
GluGlyGlyLysAspSerCysGlnGlyAspSerGlyGlyProValValCysAsnGlyGln    200
              S190A

CTCCAAGGAGTTGTCTCCTGGGGTGATGGCTGTGCCCAGAAGAACAAGCCTGGAGTCTAC    660
LeuGlnGlyValValSerTrpGlyAspGlyCysAlaGlnLysAsnLysProGlyValTyr    220
                  D217E                                V227I

ACCAAGGTCTACAACTACGTGAAATGGATTAAGAACACCATAGCTGCCAATAGCTAATGA    720
ThrLysValTyrAsnTyrValLysTrpIleLysAsnThrIleAlaAlaAsnSer******    239
                              KNTIAANS239DRSMKTR

HindIII
AGCTT
```

CHIMERIC SERINE PROTEASES

BACKGROUND OF THE INVENTION

Human serine proteases and serine proteases from mammals are involved in numerous physiological processes (Barrett, A. J., Methods in Enzymology, Vol. 244 (1994) Academic Press, New York; Twining, S. S., Crit. Revs. Biochem. Mol. Biol. 29 (1994) 315–383). These are essentially protein digestion, blood coagulation (Davie, E. W. et al., Biochemistry 20 (1991) 10363–10370), fertilization (Baba, T., FEBS Letters 27 (1989) 296–300), programmed cell death as well as complement activation in the immune response (Goldberger, G. et al., J. Biol. Chem. 262 (1987) 10065–10071). Furthermore serine proteases are known from insect cells (Gay, N. J. et al., Biochim. Biophys. Acta 1132 (1992) 290–296). from viruses (Allaire, M. et al., Nature 369 (1994) 72–76) as well as from prokaryotes. Prokaryotic serine proteases are for example subtilisin (Kraut, J., in The Enzymes (Boyer, P. D., ed.) Vol. 3, 547–560 (1971) Academic Press, New York and London), carboxypeptidase II (Liao, D. et al., Biochemistry 31 (1992) 9796–9812) and Streptomyces griseus trypsin (Read, R. J. and James, M. N. G., J. Mol. Biol. 200 (1988) 523–551).

Blood homoeostasis, the equilibrium between blood coagulation and fibrinolysis is ensured by several very complex systems which mutually influence each other. In this connection proteases play a role in blood coagulation, closure of wounds by fibrin formation as well as in fibrinolysis, i.e. clot lysis. After an injury the "injury signal" is amplified by sequential activation (specific proteolysis) of inactive proenzymes to active enzymes which initiates blood coagulation and ensures a rapid closure of wounds. Blood coagulation (haemostasis) can be initiated by two paths, the intrinsic path in which all protein components are present in the blood, and the extrinsic path in which a membrane protein, the so-called tissue factor, plays a critical role. The molecular mechanism of blood homoeostasis and the components that are involved in this has been comprehensively described in several review articles (Furie, B. et al., Cell 53 (1988) 505–518; Davie, E. W. et al., Biochem. 30 (1991) 10363–10379; Bergmeyer, H. U. (ed.): Methods of Enzymatic Analysis, Vol. V, chapter 3, 3rd ed., Academic Press, New York (1983)).

If the blood homoeostasis becomes unbalanced (blood coagulation versus fibrinolysis), an increased coagulation tendency of the blood can lead to various thrombotic disorders/diseases such as e.g. deep-vein thrombosis, pulmonary embolism, cardiac infarction and stroke (Mustard, J. F. et al., In: Haemostasis and Thrombosis. Bloom, A. L. and Thomas, D. P. (eds), 2nd edition, Churchill-Livingstone, Edinburgh, (1987) pp. 618–650). Coagulation disorders with bleeding such as e.g. in haemophilia A (defective factor VIII) and haemophilia B (defective factor IX) can occur as a result of a reduced tendency of the blood to coagulate.

There is therefore a need for substances which can influence the system of blood coagulation and fibrinolysis according to the medical needs. Factor VIII or factor IX or recently also factor VII isolated from the blood or produced recombinantly is used for example to treat haemophilia A and B. tPA (tissue type plasminogen activator) and streptokinase (bacterial plasminogen activator) are used to lyse clots for example after cardiac infarction. Antithrombotic substances (Harker, L. A. et al., In: Hemostasis and Thrombosis: Basic Principles and Clinical Praxis, Colman, R. W. et al., (eds.) 3rd edition, Lippincott, Philadelphia, (1994) pp. 1638–1660) such as e.g. hirudin (peptide composed of 65 amino acids, specific thrombin inhibitor; Maraganore, J. M., Thrombosis and Haemostasis 70 (1993) 208–211), heparin (heteroglycan, cofactor of endogenous inhibitors; Barrowcliffe, T. W. et al., In: Haemostasis and Thrombosis. Bloom, A. L. et al. (eds.); 3rd edition, Churchill-Livingstone, Edinburgh (1994) Vol. 2, pp. 1417–1438) and oral vitamin K antagonists (inhibitors of γ-carboxylation; Glu residues of the Gla domain; Hirsh, J. et al., In: Hemostasis and Thrombosis, Basic Principles and Clinical Praxis, Colman, R. W. et al., (eds.), 3rd edition, Lippincott, Philadelphia, (1994) pp. 1567–1583) are used to inhibit blood coagulation. However, the available substances are often still very expensive (protein factors) and/or not ideal with regard to their medical application and lead to considerable side effects.

All antithrombotic substances interfere with one or usually even several targets within the blood coagulation cascade. The inevitable price paid for a partial inactivation of the haemostatic system by antithrombotic substances is an increased risk of bleeding. The orally available vitamin K antagonists interfere with all vitamin K dependent coagulation factors such as e.g. the blood plasma proteases FVII, FIX, FX and thrombin which have a Gla domain that is post-translationally modified by γ-carboxylation. Consequently this antithrombotic therapy is very unspecific and influences the intrinsic as well as the extrinsic haemostatic system. Like the vitamin K antagonists, heparin interferes with several targets within the blood coagulation cascade. The antithrombotic action is due to an increased inactivation of for example thrombin, FIXa and FXa by an increased rate of formation of the complex with the natural inhibitor antithrombin III. Even the specific thrombin inhibitor hirudin derived from the leech has failed in clinical studies due to frequently occurring bleeding. There is therefore a need for new selective and better tolerated antithrombotic substances with an improved benefit to side effect ratio. In this connection the inhibition of the FXa mediated activation of prothrombin to thrombin by specific FXa inhibitors appears to be an attractive target.

The search for new modulators (activators, inhibitors) of blood coagulation, fibrinolysis and homoeostasis can be carried out by screening libraries of substances and optionally subsequently improving an identified lead structure by drug modelling. For this it is necessary that the serine proteases according to the invention are available in a crystalline form.

Attractive targets within blood homoeostasis are for example the activated serine proteases thrombin, FVIIa, FIXa, FXa, FXIa, FXIIa, kallikrein (blood coagulation), tPA, urokinase, plasmin (fibrinolysis) and activated protein C (regulatory anticoagulant) and inactive precursors (zymogens) thereof. Furthermore the complexes which form by interaction between a blood plasma protease and cofactor during blood homoeostasis such as for example FXa::FVa, FIXa::FVIIIa, thrombin::thrombomodulin, FVII/FVIIa::tissue factor are also of interest as a target.

Serine proteases can be produced recombinantly by biotechnological methods. Examples of this are human tissue plasminogen activator, urokinase and subtilisin. However, it has turned out that the serine proteases isolated from natural sources as well as those produced recombinantly do not fulfil all requirements with regard to substrate specificity, stability and purity that are needed for therapeutic applications or when they are used to cleave fusion proteins in biotechnological production processes. In particular the serine proteases factor Xa and kexin (kex 2) are very unstable. Proteases isolated from animal and/or human raw materials such as e.g. trypsin, thrombin, factor IXa and factor Xa are problematic for a therapeutic application or for an application in a production process for therapeutics since they may be contaminated with human pathogenic agents such as e.g. viruses and/or prions.

Moreover proteases isolated from animal and/or microbial raw materials are very often additionally contaminated with undesired host cell proteases. For this reason the trypsin from animal raw materials that is used to process insulin is treated with L-1-tosylamide-2-phenyl-ethyl-chloromethyl ketone (TPCK) (Kemmler, W. et al., J. Biol. Chem. 246 (1971) 6786–6791) in order to inhibit the chymotrypsin activity in these preparations. Factor Xa preparations are usually contaminated with thrombin In the purification of lysyl endoproteinase from lysobacter, the α-lytic protease has to be separated by very complicated process steps.

SUMMARY OF THE INVENTION

A chimeric protein comprising a first sequence and a second sequence C-terminal to the first sequence and linked to the first sequence by one or more peptide bonds, the first sequence having the amino acid sequence of the first catalytic domain half of a first serine protease and the second sequence having the amino acid sequence of the second catalytic domain half of a second serine protease different from the first serine protease.

BRIEF DESCRIPTION OF THE FIGURES

FIG. 2: shows the nucleotide and derived amino acid sequence of the FXT base gene. Additional mutations introduced into the N-terminal FXa half-side and into the C-terminal trypsin half-side are underlined (FXT-M variant). (The nucleotide sequence is shown in SEQ ID NO:12)

DETAILED DESCRIPTION OF THE INVENTION

Serine proteases contain a catalytic domain having β-folded sheet structure. The invention concerns a chimeric serine protease which contains a protease domain in which the protease domain is composed of two domain halves (half-sides) with a β-folded sheet structure (β-barrel architecture) and where the first domain half corresponds to the first domain half of a first serine protease and the second domain half corresponds to the second domain half of a second serine protease.

According to the invention a first domain half is understood as the domain half which is located N-terminally and the second domain half is understood as the domain half that is located C-terminally.

A chimeric serine protease of this invention is a chimera of any two serine proteases. However, the subgroup of the chymotrypsin family (See Rawlings, N. D. et al., Methods Enzymol. 244 (1994) 19–61) is preferred. In an embodiment of this invention the first sequence has the amino acid sequence of the first catalytic domain half of a serine protease selected from the group consisting of factor VII, factor VIIa, factor IX, factor IXa, factor X, factor Xa, tissue plasminogen activator, urokinase, and plasmin. In a specific embodiment, the first sequence has the amino acid sequence of the first catalytic domain half of factor Xa. Preferably the second sequence has the amino acid sequence of the second catalytic domain half of trypsin. In a specific embodiment of this invention the first sequence has the amino acid sequence of the first catalytic domain half of factor Xa and the second sequence has the amino acid sequence of the second catalytic domain half of trypsin.

In addition to the catalytic domain, a serine protease can have additional N-terminal domains. This invention encompasses chimeric proteins without these additional domains and chimeric proteins with an additional domain. In an embodiment of this invention the chimeric protein further comprises an activation peptide sequence N-terminal to the first sequence. The activation peptide sequence can be a naturally occurring or non-naturally occurring activation sequence. It can also be a fragment of a naturally occurring serine protease having activation peptide activity. Generally such fragments are from 5 to 8 amino acids in length. In a specific embodiment of this invention the activation peptide is a human trypsin activation peptide (SEQ ID NO:13). In another specific embodiment it is a truncated trypsin activation peptide, for example one having the sequence Asp-Asp-Asp-Asp-Lys.

In a specific embodiment of this invention, the chimeric protein has the amino acid sequence shown in FIG. 2.

The chimeric protein of this invention can be made by any conventional means, including chemical synthesis or recombinant techniques. Such techniques are well known in the art. When made recombinantly an expression vector which encodes the chimeric protein and is capable of expressing the protein is constructed and then transformed or transfected into a prokaryotic or eukaryotic host cell. Such techniques are well known in the art. See for example, Sambrook, J. et al., (1989) Molecular Cloning: A Laboratory Manual (Cold Spring Harbor). Starting with a known protein sequence one can determine one or more nucleic acid sequences which encode the protein based upon the genetic code (See, e.g. Lewin, Genes, 3d ed. (Wiley 1987) p. 104). This invention provides a process for recombinantly producing the protein of this invention, comprising expressing the protein in a host cell which contains an expression vector comprising a nucleic acid sequence which codes for the protein wherein the nucleic acid sequence is under the transcriptional control of a transcription control element, and isolating the expressed protein.

It has surprisingly turned out that chimeric serine proteases in which both of their protease domain halves are derived from different serine proteases essentially show a mixed substrate and binding activity, P1 specificity being determined by the C-terminal half-side, the P2 specificity by the N-terminal half-side and the P3 and P4 specificity by the N- and/or C-terminal half-side. The combination of two different complete protease domain halves (half-sides) ensures that functional subdomains (S1, S2, S3 and S4 binding pocket) can form (Perona, J. J. et al., Protein Science 4 (1995) 337–360).

Furthermore it has turned out that chimeric proteases can be obtained according to the invention which, in contrast to one or both initial proteases, can be more easily crystallized and consequently considerably facilitate structural examinations. It is for example known that human and animal trypsins crystallize well.

The crystallization of trypsin alone or in a complex with an inhibitor is state of the art (see Protein Data Base (PDB);

Bernstein, F. C. et al., J. Mol. Biol. 112 (1977) 535–542); Kurinov, I. V. et al., Protein Science 5 (1996) 752–758; Stubbs, M. et al. FEBS Letters 375 (1995) 103–107; Von der Saal, W. et al., "Archiv der Pharmazie" 329 (1996) 73–82). Numerous high resolution trypsin structures are known such as for bovine trypsin (Huber, R. et al., J. Mol. Biol. 89 (1974) 73–101), porcine trypsin (Huang, Q. et al., J. Mol. Biol. 229 (1993) 1022–1036, rat trypsin (Perona, J. J. et al., J. Mol. Biol. 230 (1993) 919–933) and human trypsin I (Gaboriaud, C. et al., J. Mol. Biol. 259 (1996) 995–1010).

The blood coagulation factor Xa (FXa) is, like thrombin, an extremely interesting target for screening, to find substances which modulate blood coagulation and especially those with an antithrombotic effect.

A prerequisite for a specific optimization by structure-based drug design of for example a low molecular FXa inhibitor lead structure identified by primary screening is the preparation. of FXa lead structure complexes and determination of their spatial structure.

Although the 3D structure of a truncated form of FXa (the Gla FXa) has recently been resolved directly (Padmanabhan, K. et al., J. Mol. Biol. 232 (1993) 947–966) and indirectly in a complex with the inhibitor DX-9065a (Brandstetter, H. et al., J. Biol. Chem. 271 (1996) 29988–29992), the more comprehensive co-crystallization experiments with other FXa inhibitors (lead structures) have previously failed due to the extremely complicated, laborious and poorly reproducible crystallization/co-crystallization of FXa. Thus, this invention also provides the chimeric proteins described above in crystalline form.

Surprisingly it was found that a chimeric protease according to the invention containing or comprising the protease domain 1 of factor Xa and protease domain 2 of trypsin can be renatured and is enzymatically active, and is similar to FXa with regard to substrate specificity ($k_{cat}/k_m$) and, like trypsin, can readily be crystallized in a complex with a ligand (such as for example with an FXa inhibitor).

Consequently the invention also concerns the use of the chimeric proteases according to the invention
i) to screen for modulators (activators and inhibitors) or
ii) to prepare crystals and/or co-crystals composed of chimeric protease and modulator.

Such crystals or co-crystals can be used advantageously for X-ray structural analysis and/or structure-based drug design.

Thus, this invention also provides the chimeric proteins described herein in crystalline form. This invention also provides a process for obtaining crystal structure data comprising crystallizing a chimeric protein according to this invention, performing x-ray crystallography on the resulting crystalline protein to produce x-ray crystal structure data, and collecting the x-ray crystal structure data.

This invention also provides a method of identifying a substance having serine protease inhibiting activity, comprising the following steps: a) contacting the chimeric protein of this invention with a target substance under conditions such that the protein of this invention would exhibit serine protease activity in the absence of the target substance; b) detecting whether the serine protease activity of the protein contacted by the target substance is decreased relative to the serine protease activity of the protein in the absence of the target substance; and c) if a decrease in serine protease activity is detected, determining that the target substance has serine protease inhibiting activity. Decreased protease activity in this assay means that the target substance has serine protease inhibitory activity.

This invention provides a process for the production of a substance with antithrombotic action, wherein a chimeric serine protease as described herein is contacted with a target substance; the effect of the target substance on the activity of the said serine protease is determined; in the case that the target substance inhibits the activity of the said serine protease, the target substance is isolated and its composition is identified; and the target substance identified in such a way is synthesized in an amount which is adequate for a therapeutic application.

The spatial structure of many serine proteases is described in detail by Lesk, A. M. et al., J. Mol. Biol. 258 (1996) 501–537 and Perona, J. J. et al., Protein Science 4 (1995) 337–360. According to them a serine protease domain is composed of two homologous structures (half sides, protease domain halves) which are presumed to be formed by gene duplication and modification. These two domains (half-sides, protease domain halves) are usually packed asymmetrically in the serine proteases and the catalytic binding site is located between these two domains. Each of these domains has a β-barrel architecture. The domains are usually composed of 6–10 antiparallel β-folded sheet strands which are folded into a β-barrel (Murzin, A. G. et al., J. Mol. Biol. 236 (1994) 1369–1381 and 1382–1400). A. M. Lesk (1996) refers to the N-terminal domain of these serine proteases as domain 1 and the C-terminal domain as domain 2. Lesk, A. M. et al. (1996) also describe the domain compositions for some exemplary serine proteases.

Usually domain 1 extends up to about amino acid position 122±5 (numbering according to the chymotrypsin numbering of J. Greer, Proteins Struct. Funct. Genet. 7 (1990) 317–334). Domain 2 begins at about amino acid position 122±5. The domain border is such that short intermediate regions can indeed exist which can either be allocated to domain 1 or to domain 2.

This invention is also concerned with the use of such chimeric proteases for the proteolytic cleavage of proteins.
Factor X Factor X is a complex glycosylated protease. It belongs mechanistically to the serine protease family. FX is synthesized in the liver as an inactive proenzyme (zymogen), secreted into the blood and is activated when required by specific proteolysis. With respect to the protein domain arrangement the structure of factor X is analogous to that of factor VII, IX and protein C. Furthermore the amino acid sequences of these 4 proteases are very homologous (amino acid sequence identity: ca. 40%). They are united in a protease subfamily, the factor IX6family.

According to Furie, B. and Furie, B. C. the proteases of the factor IX family (factor VII, IX, X and protein C) are composed of a propeptide a GLA domain an aromatic amino acid stack domain two EGF domains (EGF1 and EGF2)

a zymogen activation domain (activation peptide, AP) and a catalytic protease domain (CD).

Furthermore the blood plasma proteases are post-translationally modified during secretion:

11–12 disulfide bridges

N-glycosylation and/or O-glycosylation (GLA domain and activation peptide) (Bharadwaj, D. et al., J. Biol. Chem. 270 (1995) 6537–6542, Medved, L. V. et al., J. Biol. Chem. 270 (1995) 13652–13659)

cleavage of the propeptide

γ-carboxylation of Glu residues (GLA domain)

β-hydroxylation of an Asp residue (EGF domains).

After activation of the zymogens (zymogenic form of the protein) by specific cleavage of one or two peptide bonds (cleavage of an activation peptide), the enzymatically active proteases are composed of 2 chains which, in accordance with their molecular weight are referred to as the heavy and light chain. In the factor IX protease family the two chains are held together by an inter-molecular disulfide bridge between the EGF 2 domain and the protease domain. The zymogen-enzyme transformation (activation) leads to conformation changes within the protease domain. This enables an essential salt bridge required for the protease activity to form between the $\alpha$-$NH_3^+$ group of the N-terminal amino acid of the protease domain and an Asp residue within the FXa protease domain. The N-terminal region is very critical for this subgroup of serine proteases and should not be modified. Only then is it possible for the typical active site of serine proteases to form with the catalytic triad Ser, Asp and His (Blow, D. M.: Acc. Chem. Res. 9 (1976) 145–152; Polgar, L.: In: Mechanisms of protease action. Boca Raton, Fla., CRC Press, chapter 3 (1989)).

The FX activation peptide processing already begins in the cell during secretion (first cleavage between the EGF2 domain and the activation peptide). Then FX is activated to FXa by a second FIXa or FVIIa catalysed cleavage on the membrane in a complex with cofactor FVIIIa or tissue factor (Mann, K. G. et al., Blood 76 (1990) 1–16).

The catalytic domain of FXa is composed of 254 amino acids, is not glycosylated and forms 4 disulfide bridges. It is structurally composed of 2 barrel-like β-folded sheets, the so-called half-sides. The first half-side extends according to the chymotrypsinogen numbering from amino acid position 195 to 301 and the second half-side extends from amino acid position 302 to 448 (Greer, J., Proteins Struct. Funct. Genet. 7 (1990) 317–334; McLachlan, A. D., J. Mol. Biol. 128 (1979) 49–79; Lesk, A. D. et al., J. Mol. Biol. 258 (1996) 501–537).

The recombinant production of truncated post-translationally non-modified blood plasma protease variants of the factor IX family (factor VII, IX, X and protein C) comprising the EGF2 domain, activation peptide (AP) and catalytic domain (CD) by expression of the corresponding genes in *E. coli* and subsequent renaturation and activation of the inactive protease proteins in vitro is described comprehensively in PCT/EP97/03027.

Trypsin

The trypsin proteases are formed in the exocrine acinus cells of the pancreas as inactive proenzymes (zymogens), the so-called trypsinogens. Four different trypsinogens (trypsinogen I, II, III and IV) have been isolated from human pancreatic juice, enzymatically characterized and the amino acid sequences have been determined. The two trypsinogen genes that are expressed most strongly TRYI (trypsinogen I) and TRYII (trypsinogen II) are known. They have been isolated by cloning the corresponding cDNAs (Emi, M. et al., Gene 41 (1986) 305–310). The human trypsinogen genes TRYI and TRYII code, in accordance with a secreted protein, for a common signal peptide of 15 amino acids. This is followed by a prosegment that is characteristic for the trypsinogen genes which, in the case of the human trypsinogens I and II, is composed of the N-terminal activation peptide AlaProPheAspAspAspAspLys (SEQ ID NO:13) (Guy, O. et al., Biochem. 17 (1978) 1669–1675). This prosegment is recognized by enterokinase which is a glycoprotease secreted into the small intestine by the mucosa cells of the small intestine and cleaved in the presence of calcium which converts the inactive trypsinogens into their active form, the trypsins. Part of the trypsinogen activation occurs autocatalytically. However, cleavage by enterokinase is more than 1000 times faster.

Like factor Xa, the trypsins belong to the family of serine proteases. Activation of the trypsinogens by cleavage of the N-terminal activation peptide also in this case leads to a conformation change within the protease domain with involvement of the free N-terminus (formation of an essential salt bridge between the $\alpha$-$NH_3^+$ group of the N-terminal amino acid of trypsin and the Asp194 residue within the protease domain) which enables formation of the typical active site for serine proteases with the catalytic triad Ser, Asp and His.

The human trypsinogen I gene (TRYI), which is the most strongly expressed, codes for 247 amino acids including a signal sequence of 15 amino acids and an activation peptide of 8 amino acids. The mature trypsin I isoenzyme is thus composed of 224 amino acid residues. It contains 10 cysteine residues which form 5 disulfide bridges (Emi, M. et al., Gene 41 (1986) 305–310)). Like factor FXa the catalytic domain of trypsin is composed structurally of two "barrel-like" β-folded sheets. The first half-side extends according to the chymotrypsinogen numbering from amino acid position 16 to 121 and the second half-side from amino acid position 122 to 246 (Greer, J., Protein Struct. Funct. Genet 7 (1990) 317–334; Lesk, A. D. et al., J. Mol. Biol. 258 (1996) 501–537).

The human trypsin isoenzyme I has a sequence homology of 89% to human trypsin isoenzyme II, a sequence homology of ca. 75% to bovine trypsin and a sequence homology of ca. 43% to the catalytic domain of human factor Xa.

Chimeric Factor X/trypsin Proteases (rFXT)

Figure 1:
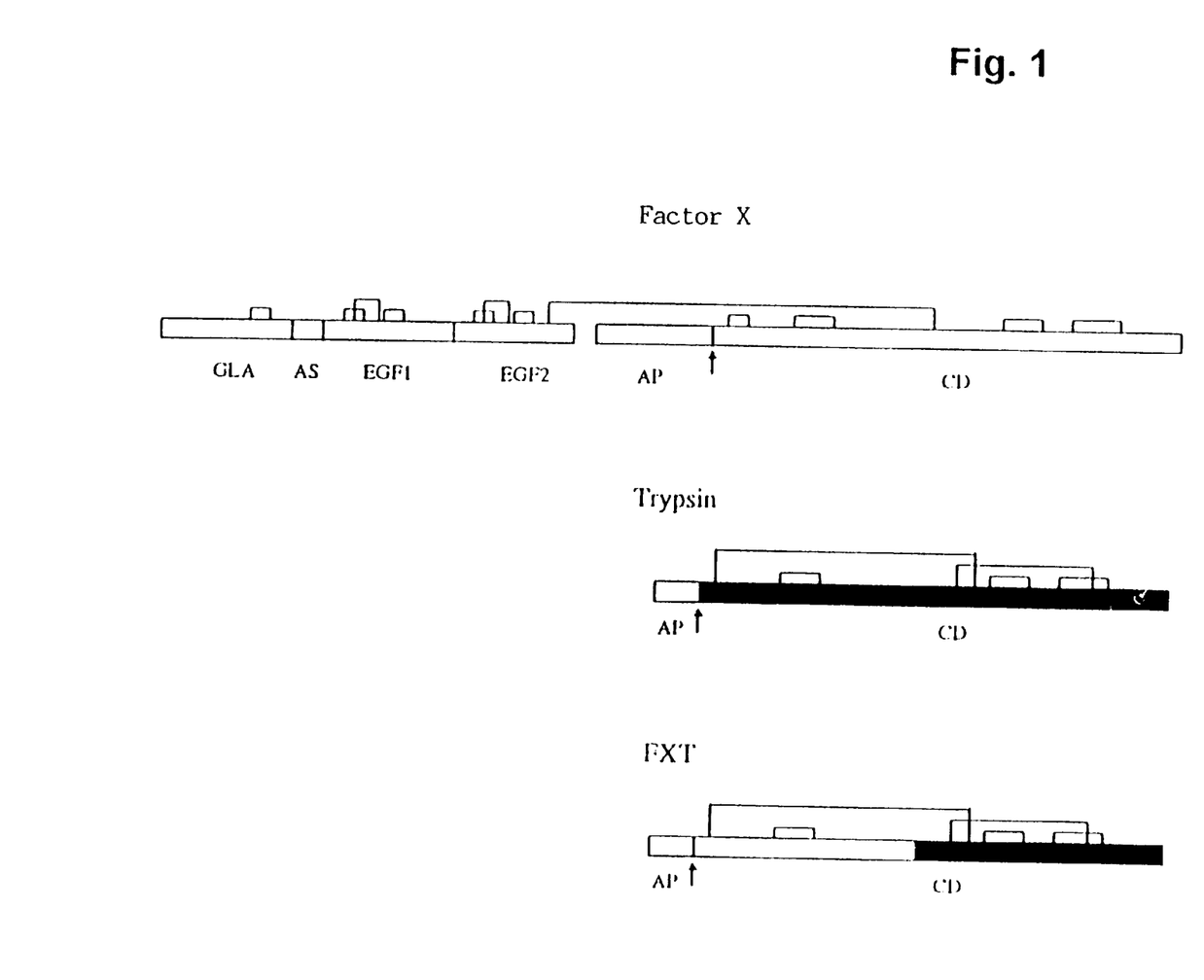
FIG. 1: Schematic representation of factor X, trypsin and the chimeric rFXT protease constructed from trypsinogen and FX. FXa parts: shown in black, trypsin parts: shown in white. Abbreviations: AP, activation peptide: AA, aromatic amino acid stack domain; CD, catalytic domain; EGF1, epidermal growth factor-like domain; EGF2, epidermal growth factor-like domain; GLA, domain rich in γ-carboxyglutamic acid residues.

FX, trypsinogen and the chimeric rFXT protease are shown schematically in FIG. 1. The basic version of the hybrid rFXT protease is composed of the N-terminal half-side of the catalytic FXa domain from amino acid position 217 to 320 (amino acid sequence numbering corresponds to the publication of Kaul, R. K. et al. (Gene 41 (1986) 311–314) and the C-terminal half-side of the catalytic trypsin domain from amino acid position 127 to 247 (amino acid sequence numbering corresponds to the publication of Emi, M. et al., Gene 41 (1986) 305–310). The FXT gene additionally codes for an N-terminal prosegment with the amino acid sequence MHHHHDDDDK (SEQ ID NO:14). It begins with an ATG start codon, this is followed by a poly-His sequence of 4 histidine residues and it ends with a truncated trypsin activation peptide (enterokinase cleavage site). The N-terminal (FXa) and C-terminal half-side (trypsin) of the rFXTa base version were constructed to be more trypsin-like or FXa-like by the introduction of further mutations. The following modifications were carried out according to the invention (FXa half-side: QE20YN, C27V; trypsin half-side: W141F, YPGK172SSFI, S190A, D217E, V227I and KNTIAANS239DRSMKTR; chymotrypsinogen numbering corresponds to Greer, J., Proteins Struct. Funct. Genet. 7 (1990) 317–334).

SEQ ID NO: 1–11 primer N1-N11
SEQ ID NO:12 shows the nucleotide sequence of the FXT base gene (accord. to FIG. 2)

SEQ ID NO:13 activation peptide of human trypsin genes I and II

SEQ ID NO:14 prosegment with truncated trypsin activation peptide

The contents of European Patent Application No. 97121232.9, filed Dec. 3, 1997 are incorporated herein by reference.

The invention will be better understood by reference to the following examples, which are illustrative of the invention but do not limit the invention as described herein and defined by the claims.

EXAMPLES

Methods

Recombinant DNA Technique

Standard methods were used to manipulate DNA as described in Sambrook, J. et al., (1989) In: Molecular cloning: A laboratory manual. Cold Spring harbor Laboratory Press, Cold Spring Harbor, N.Y. The molecular biological reagents were used according to the manufacturer's instructions.

Protein Determination

The protein concentration of the protease variants was determined by determining the optical density (OD) at 280 nm using the molar extinction coefficients calculated on the basis of the amino acid sequence.

Expression Vector

The vector for the expression of the chimeric rFXT proteases is based on the expression vector pSAM-CORE for core streptavidin. The preparation and description of the plasmid pSAM-CORE is described in WO 93/09144. The core streptavidin gene was replaced by the desired protease variant gene in the pSAM-CORE vector.

Factor Xa

The cloning of the FX gene and the construction of the plasmid pFX-EK-CD (base vector for the construction of the FXT gene) is described in detail in PCT/EP97/03027. The FX expression unit on the plasmid pFX-EK-CD codes for the N-terminal amino acid sequence MHHHHDDDDK (SEQ ID NO:14—prosegment with a truncated trypsin activation peptide) and the catalytic domain of human factor Xa.

Example 1

Cloning of the Human Trypsinogen I Gene (Plasmid: pTRYI)

The trypsinogen I cDNA from bp position 61 to 750 coding for trypsinogen I from amino acid position 19 to 247 (cDNA sequence and amino acid sequence numbering according to the publication of Emi, M. et al., (Gene 41 (1986) 305–310)) was amplified as template DNA in a polymerase chain reaction (PCR) according to the method of Mullis, K. B. et al., (Methods Enzymol. 155, (1987) 350–355) using the PCR primers N1 (SEQ ID NO:1) and N2 (SEQ ID NO:2)

```
                NcoI
N1:  5'-AAAAAACCATGGATGATGATGACAAGATCGTTGGG-3'
                  MetAspAspAspAspLysIleValGly

HindIII
N2:  5'-AAAAAAAAGCTTCATTAGCTATTGGCAGCTATGGTGTTC-3'
``` and a commercially available human liver cDNA gene bank (vector: Lambda ZAP® II) from the Stratagene Company (La Jolla, Calif., U.S.A.). The PCR primers introduced a singular NcoI cleavage site and an ATG start codon at the 5' end of the coding region and a singular HindIII cleavage site at the 3' end of the coding region.

The ca. 715 bp long PCR product was digested with the restriction endonucleases NcoI and HindIII and the ca. 700 bp long NcoI/HindIII trypsinogen I fragment was ligated into the ca. 2.55 kbp long NcoI/HindIII-pSAM-CORE vector fragment after purification by agarose gel electrophoresis. The preparation and description of the plasmid pSAM-CORE is described in WO 93/09144. The desired plasmid pTRYI was identified by restriction mapping and the TRPI cDNA sequence isolated by PCR was checked by DNA sequencing.

Example 2

Construction of the Chimeric Protease Gene FXT (Plasmid: pFXT)

The basic version of the chimeric FX/trypsin protease (name: protease rFXT; FIG. 2) is composed of a prosegment with the amino acid sequence MHHHHDDDDK (ATG-start codon, poly-His sequence and a truncated trypsin activation peptide (enterokinase cleavage site)), the N-terminal half-side of the catalytic FXa domain and the C-terminal half-side of the catalytic trypsin domain. The N-terminal FXa half-side was made more trypsin-like by introducing two further modifications (QE20YN, C27V; chymotrypsin numbering according to Greer, J., Proteins Struct. Funct. Genet. 7 (1990) 317–334).

For this purpose the DNA coding for the N-terminal half side of the catalytic FXa domain from amino acid position 217 to 320 (amino acid sequence numbering according to the publication of Kaul, R. K. et al. (Gene 41 (1986) 311–314) was amplified as template DNA using the PCR primers N3 (SEQ ID NO:3) and N4 (SEQ ID NO:4)

```
                    NsiI
N3: 5'-AAAAAAATGCATCACCACCACGACGATGACGACAAGATCGTGGGAGGC
            MetHisHIsHIsHIsAspAspAspAspLysIleValGlyGly

TAcaAcTGCAAGGACGGGGAGgtaCCCTGGCAGGCCCTGCTCATC-3'
     TyrAsnCysLysAspGlyGluValProTrpGlnAlaLeuLeuIle Van91I
N4: 5' AAAAAACCAGTGGCTGGAGGGGCGGTGGGCAGAGAGGCAGGCGCCACGTTCATGCG-3'
``` and the plasmid pFX-EK-CD (preparation and description see: PCT/EP97/03027). A DNA sequence coding for the prosegment MHHHHDDDDK with a singular NsiI cleavage site at the 5' end was introduced by means of the 5' overhanging end of the PCR primer N3. In addition the two desired mutations QE20YN and C27V were introduced into primer N3. The mutations in the primers are shown by the bases written in lower cases. The FXa DNA was linked to the trypsin DNA sequence by means of the PCR primer N4. The 5' overhanging nucleotide sequence of the N4 primer is composed of the trypsin DNA sequence from bp position 385 to 413 according to the publication of Emi, M. et al. (Gene 41 (1986) 305 to 310) with a singular Van91I cleavage site at the 5' end (shown in bold type).

The ca. 390 bp long PCR product was digested with the restriction endonucleases NsiI and Van91I and the ca. 380 bp long NsiI/Van91I N-terminal half-side fragment was purified by agarose gel electrophoresis.

The DNA coding for the C-terminal half-side of the catalytic trypsin domain from amino acid position 127 to 247 (amino acid sequence numbering according to the publication of Emi, M. et al., Gene 41 (1986) 305–310) was isolated from the plasmid pTRYI (example 1) as a ca. 360 bp long NsiI/HindIII fragment. Afterwards the NsiI/Van91I-FXa half-side fragment was ligated with a Van91I/HindIII trypsin half side fragment and inserted into the ca. 2.55 kbp long NsiI/HindIII-pFX-EK-CD vector fragment (preparation and description see: PCT/EP97/03027) in a three fragment ligation. The desired plasmid pFXT was identified by restriction mapping and the DNA sequence amplified by PCR was verified by DNA sequencing.

Example 3
Construction of the Chimeric Protease Gene FXT-M (Plasmid: pFXT-M)

The C-terminal trypsin half-side of the chimeric rFXT protease was made more FXa-like by introducing 6 mutations (W141F, YPGK172SSFI, S190A, D217E, V227I and KNTIAANS239DRSMKTR; chymotrypsinogen numbering according to Greer, J., Protein Struct. Funct.Genet. 7 (1990) 317–334).

The desired mutations were introduced into the FXT gene by two and three fragment ligations (plasmid pFXT, example 2) using enzymatically synthesized DNA fragments (PCR technique) and a chemically synthesized DNA fragment (adaptor). The DNA adaptor has a singular restriction cleavage site at the 5' and 3' end. It was prepared from 2 complementary oligonucleotides by annealing (reaction buffer: 12.5 mmol/l Tris-HCl, pH 7.0, and 12.5 mmol/l $MgCl_2$; oligonucleotide concentration: in each case 1 pmol/60 ml).

| Mutation | Oligonucleotide | Cloning cleavage sites/ fragment | length |
|---|---|---|---|
| QE20YN | N3 see example 2<br>N4 | NsiI/Van91I | ca. 380 Bp |
| C27V | N3 see example 2<br>N4 | NsiI/Van91I | ca. 380 Bp |
| W141F | N5 | Van91I/SapI | ca. 283 Bp |
| D217E | N6 | | |
| V227I | N7 adaptor | SapI/HindIII | ca. 71 Bp |
| KNTIAANS239DRSMKTR | N8 | | |
| | N5 | Van91I/SapI | ca. 157 Bp |
| YPGK172SSFI | N9 | | |
| | N10 | SapI/HindIII | ca. 198 Bp |
| S190A | N11 | | |

N5: SEQ ID NO: 5)
    Van91I
5'-AAAAAA<u>CCAGCCACTGG</u>CACGAAGTGCCTCATCTCTGGCTtcGGCAACACTGCGCAGCTCTGGCG-3'

N6: (SEQ ID NO: 6)
    SapI
5'-AAAAAA<u>GCTCTTC</u>CTCCAGGCTTGTTCTTCTGGCACAGCCtTCACCCCAGGAGACAACTCCTTG-3'

N7: (SEQ ID NO:7)
    SapI
5'-AAAAAA<u>GCTCTTC</u>TGGAaTCTACACCAAGGTCTACAACTACGTGAAATGGATTgaccgt
                      TyrThrLysValTyrAsnTyrValLysTrpIle<u>AspArg</u>

HindIII
   tCtatgaaaaCCcgTtaatg<u>AAGCTT</u>TTTTTT-3'
   <u>SerMetLysThrArg</u>******

N8: (SEQ ID NO: 8)
    HindIII
5'-AAAAAA<u>AAGCTT</u>cattaAcgGGttttcataGaacggtcAATCCATTTCACGTAGTTGTA                    SapI
   GACCTTGGTGTAGAtTCCA<u>GAAGAGC</u>TTTTTT-3'

N9: (SEQ ID NO: 9)
    SapI
5'-AAAAAA<u>GCTCTTC</u>CACAGAACATGTTGCTGGTAATgaTgaaggaagAGGAGGCTTCACAC
   TTAGCCTGGC-3'

-continued

| Mutation | Oligonucleotide | Cloning cleavage sites/ fragment | length |
|---|---|---|---|

N10: (SEQ ID NO: 10)
     SapI
5'-AAAAAAGCTTCTTCCTGTGTGGGCTTCCTTGAGGGAGGCAAGGATgCtTGTCAGGG
   TGATTCTGGTGG-3'

N11: (SEQ ID NO: 11)
     HindIII
5'-AAAAAAAAGCTTCATTAACGGGTTTTCATAGAACGGTCAATCCATTTCACGTAG-3'

The desired intermediate constructs and the pFXT-M final construct were identified by restriction mapping. The desired DNA sequence of the FXT-M mutant gene (final construct) was confirmed by DNA sequencing.

Example 4 a) Expression of the Chimeric FXT Protease Gene in E. coli

In order to express the FXT gene an E. coli K12 strain (e.g. UT5600, Grodberg, J. et al., J. Bacteriol. 170 (1988) 1245–1253) was transformed with one of the expression plasmids pFXT and PFXT-M (ampicillin resistance) described in examples 2 and 3 and with the lacI$^q$ repressor plasmid pUBS520 (Kanamycin resistance, preparation and description see: Brinkmann, U. et al., Gene 85 (1989) 109–114).

The UT5600/pUBS520/cells transformed with the expression plasmids pFXT and pFXT-M were cultured at 37° C. up to an optical density at 550 nm ($OD_{550}$) of 0.6–0.9 in a shaking culture in DYT medium (1% (w/v) yeast extract, 1% (w/v) Bacto Tryptone, Difco and 5% NaCl) containing 50–100 mg/l ampicillin and 50 mg/l kanamycin and subsequently induced with IPTG (final concentration 1–5 mmol/l). After an induction phase of 4–8 hours (h) at 37° C., the cells were harvested by centrifugation (Sorvall RC-5B centrifuge, GS3 rotor, 6000 rpm, 15 min), washed with 50 mmol/l Tris-HCl buffer pH 7.2 and stored at −20° C. until further processing. The cell yield from a 1 l shaking culture was 4–5 g (wet weight).

b) Expression Analysis

The expression of the UT5600/pUBS520/cells transformed with the plasmids pFXT and pFXT-M was analysed. For this purpose cell pellets from in each case 1 ml centrifuged culture medium were resuspended in 0.25 ml 10 mmol/l Tris-HCl, pH 7.2 and the cells were lysed by ultrasonic treatment (2 pulses of 30 s at 50% intensity) using a Sonifier® Cell Disruptor B15 from the Branson Company (Heusenstamm, Germany). The insoluble cell components were sedimented (Eppendorf 5415 centrifuge, 14000 rpm, 5 min) and 1/5 volumes (vol) 5×SDS sample buffer (1×SDS sample buffer: 50 mmol/l Tris-HCl, pH 6.8, 1% SDS, 1% mercaptoethanol, 10% glycerol, 0.001% bromophenol blue) was added to the supernatant. The insoluble cell debris fraction (pellet) was resuspended in 0.3 ml 1×SDS sample buffer containing 6–8 M urea, the samples were incubated for 5 min at 95° C. and centrifuged again. Afterwards the proteins were separated by SDS polyacrylamide gel electrophoresis (PAGE) (Laemmli, U. K., Nature 227 (1970) 680–685) and stained with Coomassie Brilliant Blue R dye.

The protease variants synthesized in E. coli were homogeneous and were exclusively found in the insoluble cell debris fraction (inclusion bodies, IBs). The expression yield was 10–50% relative to the total E. coli protein.

Example 5

Cell lysis, solubilization and renaturation of the chimeric rFXT proteases a) Cell Lysis and Preparation of Inclusion Bodies (IBs)

The cell pellet from 3 l shaking culture (ca. 15 g wet weight) was resuspended in 75 ml 50 mmol/l Tris-HCl, pH 7.2. The suspension was admixed with 0.25 g/ml lysozyme and it was incubated for 30 min at 0° C. After addition of 2 mmol/l $MgCl_2$ and 10 mg/ml DNase I (Boehringer Mannheim GmbH, catalogue No. 104159) the cells were disrupted mechanically by means of high pressure dispersion in a French® Press from the SLM Amico Company (Urbana, Ill., USA). Subsequently the DNA was digested for 30 min at room temperature (RT). 37.5 ml 50 mmol/l Tris-HCl pH 7.2, 60 mmol/l EDTA, 1.5 mol/l NaCl, 6% Triton X-100 was added to the preparation it was, incubated for a further 30 min at RT and centrifuged in a Sorvall RC-5B centrifuge (GSA Rotor, 12000 rpm, 15 min). The supernatant was discarded, 100 ml 50 mmol/l Tris-HCl, pH 7.2, 20 mmol/l EDTA was added to the pellet, it was incubated for 30 min while stirring at 4° C. and again sedimented. The last wash step was repeated. The purified IBs (1.5–2.0 g wet weight, 25–30% dry mass, 100–150 mg protease) were stored at −20° C. until further processing.

b) Solubilization and Derivatization of the IBs

The purified IBs were dissolved within 1 to 3 hours at room temperature at a concentration of 100 mg IB pellet (wet weight)/ml corresponding to 5–10 mg/ml protein in 6 mol/l guanidinium-HCl, 100 mmol/l Tris-HCl, 20 mmol/l EDTA, 150 mmol/l GSSG and 15 mmol/l GSH, pH 8.0. Afterwards the pH was adjusted to pH 5.0 and the insoluble components were separated by centrifugation (Sorvall RC-5B centrifuge, SS34 rotor, 16000 rpm, 10 min). The supernatant was dialysed for 24 hours at 4° C. against 100 vol. 4–6 mol/l guanidinium-HCl pH 5.0.

c) Renaturation

The renaturation of the protease variants solubilized in 6 mol/l guanidinium-HCl and derivatized with GSSG/GSH was carried out at 4° C. by repeated (e.g. 3-fold) addition of 0.5 ml IB solubilisate/derivative in each case to 50 ml 50 mmol/l Tris-HCl, 0.5 mol/l arginine, 20 mmol/l $CaCl_2$, 1 mmol/l EDTA and 0.5 mmol/l cysteine, pH 8.5 at intervals of 24 hours and subsequent incubation for 48 hours at 4° C. After completion of the renaturation reaction the insoluble components were separated by filtration with a filtration apparatus from the Satorius Company (Göttingen, Germany) equipped with a deep bed filter K 250 from the Seitz Company (Bad Kreuznach, Germany).

d) Concentration and Dialysis of the Renaturation Preparations

The clear supernatant containing protease was concentrated 10–15-fold by cross-flow filtration in a Minisette (membrane type: Omega 10K) from the Filtron Company (Karlstein, Germany) and dialysed for 24 hours at 4° C. against 100 vol. 20 mmol/l Tris-HCl and 50 mmol/l NaCl, pH 7.2 to remove guanidinium-HCl and arginine. Precipitated protein was removed by centrifugation (Sorvall RC-5B centrifuge, SS34 rotor, 16000 rpm, 20 min) and the clear supernatant was filtered with a Nalgene® disposable filtration unit (pore diameter: 0.2 mm) from the Nalge Company (Rochester, N.Y., USA).

Example 6

Purification of the Renatured Inactive chimeric rFXT Proteases

The inactive rFXT proteases from the renaturation preparations can, if required, be further purified with chromatographic methods which are known to a person skilled in the art.

Purification of the Chimeric rFXT Proteases by Ion Exchange Chromatography on Q-Sepharose ff The concentrated renaturation preparation that had been dialysed against 20 mmol/l Tris-HCl and 50 mmol/l NaCl, pH 8.0 was applied to a Q-Sepharose ff column (1.5×11 cm, V=20 ml; loading capacity: 10 mg protein/ml gel) from the Pharmacia Biotech Company (Freiburg, Germany) (2 column volumes/hour, 2 CV7h) equilibrated with the same buffer and it was washed with the equilibration buffer until the absorbance of the eluate at 280 nm had reached the blank value of the buffer. The bound material was eluted by a gradient of 50–500 mmol/l NaCl in 20 mmol/l Tris-HCl, pH 8.0 (2 CV/h). The proteases were eluted at an NaCl concentration of 100–150 mmol/l. The fractions containing proteases were identified by non-reducing and reducing SDS PAGE and the elution peak was pooled.

Example 7

Activation of the Chimeric rFXT Proteases with Enterokinase

The chimeric rFXT proteases were digested at 25° C. at a concentration of 0.5 to 2.0 mg/ml and a substrate/protease ratio of 50:1 to 100:1 (enterokinase, restriction protease from calf intestine, Boehringer Mannheim, Mannheim, Germany) in 50 mmol/l Tris-HCl, pH 8.0. The time course of the enzymatic rFXT activation was monitored by activity determination with a chromogenic colour substrate (see example 9b) until completion of the digestion (plateau, maximum activation). For this samples (10 to 100 ml) were taken at intervals of 5–10 minutes from the reaction mixture over a period of up to 2 hours and the generated rFXTa activity was determined. After reaching the activity plateau the enterokinase digest was purified by affinity chromatography on benzamidine-Sepharose.

Example 8

Final Purification of the Activated Chimeric rFXTa Proteases

The digestion mixture was applied (2 CV/h) to a benzamidine-Sepharose CL-6B column (1.0×10 cm, V=8 ml; loading capacity: 2–3 mg protein/ml gel) from the Pharmacia Biotech Company (Freiburg, Germany) that had been equilibrated with 20 mmol/l Tris-HCl, 200 mmol/l NaCl, pH 8.0 and washed with equilibration buffer until the absorbance of the eluate at 280 nm reached the blank value for the buffer. The bound material was eluted by 20 mmol/l Tris-HCl, 200 mmol/l NaCl, 10 mmol/l benzamidine, pH 8.0 (2 CV/h). The fractions containing rFXTa protease were identified by non-reducing and reducing SDS PAGE and activity determination.

The serine protease inhibitor benzamidine used for the elution was removed by dialysis against 20 mmol/l Tris-HCl, 200 mmol/l NaCl, pH 8.0.

Example 9

Characterization of the Purified rFXT Protease Variants a) SDS PAGE

Oligomer and aggregate formation by intermolecular disulfide bridge formation as well as the homogeneity and purity of the renatured activated and purified rFXTa proteases were examined by non-reducing (minus mercaptoethanol) and reducing (plus mercaptoethanol) SDS PAGE (Laemmli, U. K., Nature 227 (1970) 680–685).

b) Activity Determination, Determination of the Kinetic Constants

The activity of the renatured activated rFXTa proteases was determined with the chromogenic substrates Chromozym® X (N-methoxycarbonyl-D-Nle-Gly-Arg-pNA, Boehringer Mannheim GmbH, Mannheim, Cat. No. 789763), Chromozym® U (Bz-$\beta$-Ala-Gly-Arg-pNA, Boehringer Mannheim GmbH, Mannheim, Cat. No.836583), Chromozym® PK (Bz-Pro-Phe-Arg-pNA, Boehringer Mannheim GmbH, Mannheim, Cat. No. 378445) and Chromozym® TH (Tosyl-Gly-Pro-Arg-pNA, Boehringer Mannheim GmbH, Mannheim, Cat. No. 838268) in comparison with recombinant rFXa (rFX-EGF2-AP-CD; preparation and description see PCT/EP97/03027) and native human trypsin (Sigma-Aldrich Chemie GmbH, Deisenhofen, Germany, Cat. No. T6424). Abbreviations: Bz, benzoyl; pNA, p-nitroaniline.

10–100 µl sample was filled up to 200 µl with 190–100 µl 50 mmol/l Tris-HCl, 150 mmol/l NaCl, 5 mmol/l $CaCl_2$, 0.1% PEG 8000, pH 8.0 and 20 µl Chromozym® X, U, PK and TH (0.5–40 mmol/l) were added to and measured against a reagent blank value in an ELISA reader at a wavelength of 405 nm and RT. The activity and the kinetic constants were determined from the linear initial slope according to the Michaelis Menten equation.

| | kcat (1/s) | Km (µM) | kcat/Km (1/µM/s) |
|---|---|---|---|
| Chromozym ® X (N-methoxycarbonyl-D-Nle-Gly-Arg-pNA) | | | |
| rFXa | 215 | 199 | 1.1 |
| fFXTa | 52 | 22 | 2.4 |
| trypsin | 153 | 43 | 3.6 |
| Chromozym ® U (Bz-$\beta$-Ala-Gly-Arg-pNA) | | | |
| rFXa | 66 | 134 | 0.5 |
| fFXTa | 68 | 49 | 1.4 |
| trypsin | 225 | 208 | 1.1 |
| Chromozym ® PK (Bz-Pro-Phe-Arg-pNA) | | | |
| rFXa | 53 | 265 | 0.2 |
| fFXTa | 119 | 115 | 1 |
| trypsin | 38 | 17 | 2.2 |
| Chromozym ® TH (tosyl-Gly-Pro-Arg-pNA) | | | |
| rFXa | 107 | 149 | 0.7 |
| fFXTa | 39 | 23 | 1.7 |
| trypsin | 95 | 13 | 7.3 |

Bz: benzyl
BpNA: p-nitroaniline

Example 10
Crystallization of the Chimeric rFXTa Proteases

The activated purified recombinantly produced rFXTa proteases were dialysed for 6 h at 4° C. against 2×100 vol. 5 mmol/l HEPES pH 6.5 and subsequently concentrated to a concentration of 5 mg/ml in a Centrikon® 10 microconcentrator from the Amicon Company (Witten, Germany). The crystallization was carried out by vapour diffusion in a sitting drop. 4 ml of the FXa specific inhibitor DX-9065a (Katakura, S. et al., Biochem. Biophys. Res. Commun. 197 (1993) 965–972) was added to 4 ml concentrated rFXTa protease (inhibitor concentration: 0.5 mmol/l in 100 mmol/l Tris-HCl, 10% polyethylene glycol 6 K (PEG 6 K), pH 7.0) and equilibrated at 4° C. by means of vapour diffusion in the sitting drop. Crystals grew after 3–7 days.

BIBLIOGRAPHY

Allaire, M. et al., Nature 369 (1994) 72–76
Baba, T., FEBS Letters 27 (1989) 296–300
Barrett, A. J., Methods Enzymol. Vol. 244 (1994) Academic Press, New York
Barrowcliffe, T. W. et al., In: Haemostasis and Thrombosis. Bloom, A. L. et al., (eds.), 3rd edition, Churchill-Livingstone, Edinburgh, (1994) Vol. 2,pp.1417–1438
Bergmeyer, H. U. (ed.): Methods of Enzymatic Analysis, Vol. V, chapter 3, 3rd ed., Academic Press, New York (1983)
Bernstein, F. C. et al., J. Mol. Biol. 112 (1977) 535–542
Bharadwaj, D. et al., J. Biol. Chem. 270 (1995) 6537–6542
Blow, D. M.: Acc. Chem. Res. 9 (1976) 145–152; Polgar, L.: Mechanism of protease action. Boca Raton, Fla., CRC Press, chapter 3 (1989)
Brandstetter, H. et al., J. Biol. Chem. 271 (1996) 29988–29992
Brinkmann, U. et al., Gene 85 (1989) 109–114
Davie, E. W. et al., Biochemistry 30 (1991) 10363–10370
Emi, M. et al. Gene 41 (1986) 305–310
Furie, B. et al., Cell 53 (1988) 505–518
Gaboriaud, C. et al., J. Mol. Biol. 259 (1996) 995–1010
Gay, N. J. et al., Biochim. Biophys. Acta 1132 (1992) 290–296
Goldberger, G. et al., J. Biol. Chem. 262 (1987) 10065–10071
Greer, J., Proteins Struct. Funct. Genet. 7 (1990) 317–334
Grodberg, J. et al., J. Bacteriol. 170 (1988) 1245–1253
Guy, O. et al., Biochem. 17 (1978) 1669–1675
Harker, L. A. et al., In: Hemostasis and Thrombosis: Basic Principles and Clinical Praxis, Colman, R. W. et al., (eds.), 3rd edition, Lippincott, Philadelphia, (1994) pp. 1638–1660
Hirsh, J. et al., In: Hemostasis and Thrombosis: Basic Principles and Clinical Praxis, Colman, R. W. et al., (eds.), 3rd edition, Lippincott, Philadelphia, (1994) pp. 1567–1583
Huang, Q. et al., J. Mol. Biol. 229 (1993) 1022–1036
Huber, R. et al., J. Mol. Biol. 89 (1974) 73–101
Katakura, S. et al., Biochem. Biophys. Res. Commun. 197 (1993) 965–972
Kaul, R. K. et al., Gene 41 (1986) 311–314
Kemmler, W. et al., J. Biol. Chem. 246 (1971) 6786–6791
Kraut, J., In: The Enzymes (Boyer, P. D. ed.) vol. 3, 547–560 (1971) Academic Press, New York and London
Kurinov, I. V. et al., Protein Science 5 (1996) 752–758
Laemmli, U. K., Nature 227 (1970) 680–685
Lesk, A. M. et al., J. Mol. Biol. 258 (1996) 501–537
Liao, D. et al., Biochemistry 31 (1992) 9796–9812
Mann, K. G. et al., Blood 76 (1990) 1–16
Maraganore, J. M., Thrombosis and Haemostasis 70 (1993) 208–211
McLachlan, A. D., J. Mol. Biol. 128 (1979) 49–79
Medved, L. V. et al., J. Biol. Chem. 270 (1995) 13652–13659
Mullis, K. B. et al., Methods Enzymol. 155 (1987) 350–355
Murzin, A. G. et al., J. Mol. Biol. 236 (1994) 1369–1381 and 1382–1400
Mustard, J. F. et al., In: Haemostasis and Thrombosis. Bloom, A. L. and Thomas, D. P. (eds.), 2nd edition, Churchill-Livingstone, Edinburgh, (1987) pp. 618–650
Padmanabhan, K. et al., J. Mol. Biol. 232 (1993) 947–966
PCT/EP97/03027
Perona, J. J. et al., J. Mol. Biol. 230 (1993) 919–933
Perona, J. J. et al., Protein Science 4 (1995) 337–360
Polgar, L.: In: Mechanisms of protease action. Boca Raton, Fla., CRC Press, chapter 3 (1989)
Protein Data Base (PDB)
Rawlings, N. D. et al., Methods Enzymol. 244 (1994) 19–61
Read, R. J. and James, M. N. G., J. Mol. Biol. 200 (1988) 523–551
Sambrook, J. et al., (1989) In: Molecular cloning: A laboratory manual. Cold Spring Harbor Laboratory Press, Cold Spring Harbor, N.Y.
Stubbs, M. et al., FEBS Letters 375 (1995) 103–107
Twining, S. S., Crit. Revs. Biochem. Mol. Biol. 29 (1994) 315–383
Von der Saal, W. et al., Archiv der Pharmazie 329 (1996) 73–82
WO 93/09144

---

What is claimed is:

1. A chimeric protein comprising a first sequence and a second sequence C-terminal to the first sequence and linked to the first sequence by one or more peptide bonds, the first sequence having the amino acid sequence of the first catalytic domain half of a first serine protease and the second sequence having the amino acid sequence of the second catalytic domain half of a second serine protease different from the first serine protease; wherein the first sequence has the amino acid sequence of the first catalytic domain half of factor Xa and the second sequence has the amino acid sequence of the second catalytic domain half of trypsin.

2. The protein of claim 1 having the amino acid sequence corresponding to SEQ ID NO:12.

3. The protein of claim 1 in crystalline form.

* * * * *

SEQUENCE LISTING

```
<160> NUMBER OF SEQ ID NOS: 15

<210> SEQ ID NO 1
<211> LENGTH: 35
<212> TYPE: DNA
<213> ORGANISM: Artificial Sequence
<220> FEATURE:
<223> OTHER INFORMATION: Description of Artificial Sequence:primer N1

<400> SEQUENCE: 1
aaaaaaccat ggatgatgat gacaagatcg ttggg                           35
```

-continued

```
<210> SEQ ID NO 2
<211> LENGTH: 39
<212> TYPE: DNA
<213> ORGANISM: Artificial Sequence
<220> FEATURE:
<223> OTHER INFORMATION: Description of Artificial Sequence:primer N2

<400> SEQUENCE: 2
aaaaaaaagc ttcattagct attggcagct atggtgttc                              39

<210> SEQ ID NO 3
<211> LENGTH: 93
<212> TYPE: DNA
<213> ORGANISM: Artificial Sequence
<220> FEATURE:
<223> OTHER INFORMATION: Description of Artificial Sequence:primer N3

<400> SEQUENCE: 3
aaaaaaatgc atcaccacca cgacgatgac gacaagatcg tgggaggcta caactgcaag       60
gacggggagg taccctggca ggccctgctc atc                                    93

<210> SEQ ID NO 4
<211> LENGTH: 56
<212> TYPE: DNA
<213> ORGANISM: Artificial Sequence
<220> FEATURE:
<223> OTHER INFORMATION: Description of Artificial Sequence:primer N4

<400> SEQUENCE: 4
aaaaaaccag tggctggagg ggcggtgggc agagaggcag gcgccacgtt catgcg          56

<210> SEQ ID NO 5
<211> LENGTH: 64
<212> TYPE: DNA
<213> ORGANISM: Artificial Sequence
<220> FEATURE:
<223> OTHER INFORMATION: Description of Artificial Sequence:primer N5

<400> SEQUENCE: 5
aaaaaaccag ccactggcac gaagtgcctc atctctggct tcggcaacac tgcgagctct      60
ggcg                                                                    64

<210> SEQ ID NO 6
<211> LENGTH: 65
<212> TYPE: DNA
<213> ORGANISM: Artificial Sequence
<220> FEATURE:
<223> OTHER INFORMATION: Description of Artificial Sequence:primer N6

<400> SEQUENCE: 6
aaaaaagctc ttcctccagg cttgttcttc tgggcacagc cttcacccca ggagacaact      60
ccttg                                                                   65

<210> SEQ ID NO 7
<211> LENGTH: 91
<212> TYPE: DNA
<213> ORGANISM: Artificial Sequence
<220> FEATURE:
<223> OTHER INFORMATION: Description of Artificial Sequence:primer  N7

<400> SEQUENCE: 7
aaaaaagctc ttctggaatc tacaccaagg tctacaacta cgtgaaatgg attgaccgtt      60
ctatgaaaac ccgttaatga agcttttttt t                                      91
```

-continued

<210> SEQ ID NO 8
<211> LENGTH: 91
<212> TYPE: DNA
<213> ORGANISM: Artificial Sequence
<220> FEATURE:
<223> OTHER INFORMATION: Description of Artificial Sequence:primer N8

<400> SEQUENCE: 8
aaaaaaaagc ttcattaacg ggttttcata gaacggtcaa tccatttcac gtagttgtag     60
accttggtgt agattccaga agagctttt t                                    91

<210> SEQ ID NO 9
<211> LENGTH: 70
<212> TYPE: DNA
<213> ORGANISM: Artificial Sequence
<220> FEATURE:
<223> OTHER INFORMATION: Description of Artificial Sequence:primer N9

<400> SEQUENCE: 9
aaaaaagctc ttccacagaa catgttgctg gtaatgatga aggaagagga ggcttcacac     60
ttagcctggc                                                           70

<210> SEQ ID NO 10
<211> LENGTH: 67
<212> TYPE: DNA
<213> ORGANISM: Artificial Sequence
<220> FEATURE:
<223> OTHER INFORMATION: Description of Artificial Sequence:primer N10

<400> SEQUENCE: 10
aaaaaagctc ttcctgtgtg ggcttccttg agggaggcaa ggatgcttgt cagggtgatt     60
ctggtgg                                                              67

<210> SEQ ID NO 11
<211> LENGTH: 54
<212> TYPE: DNA
<213> ORGANISM: Artificial Sequence
<220> FEATURE:
<223> OTHER INFORMATION: Description of Artificial Sequence:primer N11

<400> SEQUENCE: 11
aaaaaaaagc ttcattaacg ggttttcata gaacggtcaa tccatttcac gtag           54

<210> SEQ ID NO 12
<211> LENGTH: 725
<212> TYPE: DNA
<213> ORGANISM: Homo sapiens

<400> SEQUENCE: 12
atgcatcacc accacgacga tgacgacaag atcgtgggag gccaggaatg caaggacggg     60
gagtgtccct ggcaggccct gctcatcaat gaggaaaacg agggtttctg tggtggaacc    120
attctgagcg agttctacat cctaacggca gcccactgtc tctaccaagc caagagattc    180
aaggtgaggg tagggaccgg aacacggag caggaggagg cgtgaggc ggtgcacgag       240 gtggaggtgg tcatcaagca caaccggttc acaaaggaga cctatgactt cgacatcgcc    300
gtgctccggc tcaagacccc catcaccttc cgcatgaacg tggcgcctgc ctctctgccc    360
accgcccctc cagccactgg cacgaagtgc ctcatctctg gctgggcaa cactgcgagc     420 tctggcgccg actacccaga cgagctgcag tgcctggatg ctcctgtgct gagccaggct    480
aagtgtgaag cctcctaccc tggaaagatt accagcaaca tgttctgtgt gggcttcctt    540

-continued

```
gagggaggca aggattcatg tcagggtgat tctggtggcc ctgtggtctg caatggacag    600
ctccaaggag ttgtctcctg gggtgatggc tgtgcccaga agaacaagcc tggagtctac    660
accaaggtct acaactacgt gaaatggatt aagaacacca tagctgccaa tagctaatga    720
agctt                                                                725
```

<210> SEQ ID NO 13
<211> LENGTH: 8
<212> TYPE: PRT
<213> ORGANISM: Homo sapiens

<400> SEQUENCE: 13

Ala Pro Phe Asp Asp Asp Asp Lys
 1               5

<210> SEQ ID NO 14
<211> LENGTH: 10
<212> TYPE: PRT
<213> ORGANISM: Homo sapiens

<400> SEQUENCE: 14

Met His His His His Asp Asp Asp Asp Lys
 1               5                   10

<210> SEQ ID NO 15
<211> LENGTH: 5
<212> TYPE: PRT
<213> ORGANISM: Homo sapiens

<400> SEQUENCE: 15

Asp Asp Asp Asp Lys
 1               5